United States Patent [19]

Stahly

[11] Patent Number: 5,128,066

[45] Date of Patent: Jul. 7, 1992

[54] ANTIOXIDANT AROMATIC FLUOROPHOSPHITES

[75] Inventor: G. Patrick Stahly, Baton Rouge, La.

[73] Assignee: Ethyl Corporation, Richmond, Va.

[21] Appl. No.: 522,651

[22] Filed: May 14, 1990

[51] Int. Cl.⁵ .................. C23F 11/12; C23F 11/16; C23F 11/167

[52] U.S. Cl. ...................... 252/400.24; 558/83

[58] Field of Search ............... 558/84, 83; 252/400.24

[56] References Cited

U.S. PATENT DOCUMENTS 4,867,907  9/1989  Burton et al. .................. 558/84
4,962,144  10/1990  Babillis et al. ................. 558/84

FOREIGN PATENT DOCUMENTS 0280938  9/1988  European Pat. Off. .

Primary Examiner—Deborah L. Kyle
Assistant Examiner—Valerie Fee
Attorney, Agent, or Firm—Richard J. Hammond

[57] ABSTRACT

Fluoroalkylphosphorous compounds are disclosed having the formula

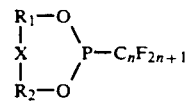

wherein $R_1$ and $R_2$ are wherein the same or different and are substituted or unsubstituted aryl groups, the substituents are selected from alkyl, aryl, the group consisting of aralkyl, cycloalkyl, hydroxy, alkoxy, aryloxy and halo; X is a single bond connecting $R_1$ and $R_2$, or X is selected from the group consisting of $C_1$ to $C_{12}$ linear or branched alkylene, —O— or —$S_g$— where g is an integer from 1 to 3; and n is an integer from 1 to 8. These compounds, when used in organic compositions susceptible to oxidative degradation act to effectively retard such degradation.

16 Claims, No Drawings

ANTIOXIDANT AROMATIC FLUOROPHOSPHITES

BACKGROUND OF THE INVENTION

1. Field of the Invention

This invention relates to aromatic fluorophosphorus compounds and their use as antioxidants in organic materials such as organic polymers.

2. Description of the Prior Art

Phosphites, phosphonites and other organic phosphorus compounds are used in organic polymers and other organic materials as antioxidants. They are generally considered better than phenolic antioxidants at high temperatures because these materials eliminate hydroperoxides which decompose and lead to autooxidation chain reactions. Thus, phosphorus compounds are important for oxidative stability during various operations including polyolefin extrusion.

Phenolic and phosphorus antioxidants are often used together in polyolefin homopolymers and copolymers to provide antioxidant protection for both low and high temperature exposure. Unfortunately, additional expense is encountered as additives in larger amounts are needed for the polymers. Thus, there exists a need for effective antioxidants at a reasonable additive price, not only for polyolefins, but other substrates as well.

It is common practice to include an antioxidant in organic materials normally susceptible to oxidative degradation. Many of the antioxidants employed have limited effectiveness or tend to impart undesirable properties to the organic material such as causing color. The problem is particularly acute with polymers and copolymers of ethylenically unsaturated monomers, especially polyolefins such as polypropylene. These materials are subjected to elevated temperatures during processing, which tends to destroy many antioxidants with the result that the polymer rapidly degenerates during use. The aromatic fluorophosphorus compounds of the present invention allow organic materials to maintain excellent color and thermal stability.

SUMMARY OF THE INVENTION

According to the present invention, certain aromatic fluorophosphorus compounds are provided which are very effective as stabilizers in a wide range of organic materials. The aromatic fluorophosphorus compounds are very effective because they retard changes in viscosity of organic materials stabilized therewith for extensive periods of time under processing conditions. In addition, they are stable when stored at room temperatures. They are especially effective when used in combination with phenolic antioxidants.

DESCRIPTION OF THE PREFERRED EMBODIMENTS

A preferred embodiment of the present invention is an organic material normally susceptible to gradual oxidative degradation when in contact with oxygen said organic material containing an antioxidant amount of an aromatic fluorophosphorus compound being characterized by having at least one benzene group bonded through oxygen to a trivalent phosphorus atom and at least one perfluoroalkyl group bonded to the same phosphorus atom.

Any organo phosphorus compound meeting the above definition is readily recognized by its structural formula. One preferred class of compounds is represented by the formula

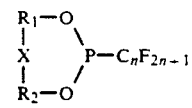

wherein $R_1$ and $R_2$ are the same or different and are unsubstituted or substituted aryl. The substituents selected from alkyl, aryl, aralkyl, cycloalkyl, hydroxy, alkoxy, aryloxy and halo; X is a single bond connecting $R_1$ and $R_2$, $C_1$ to $C_{12}$ linear or branched alkylene, —O—, or $S_g$ where g is an integer from 1 to 3; and n is an integer from 1 to 8. In a still more preferred embodiment of this class of compounds the substituents are alkyls having 1-20 carbon atoms, aryls having 6-12 carbon atoms, arylalkyls having 7-12 carbon atoms, cycloalkyls having 5-8 carbon atoms, hydroxy, alkoxy having 1-12 carbon atoms, aryloxy having 6-12 carbon atoms, halo, alkoxycarbonylalkyl having 1-20 carbon atoms in its alkoxy moiety and 1-3 carbon atoms in its alkyl moiety, alkoxy carbonyl having 1-20 carbon atoms in its alkoxy moiety and acyloxy having 1-4 carbon atoms.

Representative examples of the above substitutents are methyl, isopropyl, sec-butyl, tert-butyl, n-decyl, sec-dodecyl, sec-eicosyl, phenyl, o-tolyl, p-tolyl, naphthyl, 4-phenylphenyl, 4-sec-hexylphenyl, benzyl, alpha-methylbenzyl, phenethyl, 4-tert-butylbenzyl, 4-tert-butyl-alpha-methylbenzyl, cyclopentyl, cyclohexyl, cyclooctyl, methoxy, ethoxy, isopropoxy, 2-ethylhexoxy, 2-ethoxyethoxy, isobutoxy, dodecoxy, phenoxy, 4-ethylphenoxy, napthoxy, 4-phenylphenoxy, chloro, bromo, fluoro, iodo, methoxycarbonylmethyl, butoxycarbonylethyl, dodecyloxycarbonylpropyl, octadecyloxycarbonylethyl, icosyloxycarbonylethyl, methoxycarbonyl, butoxycarbonyl, decyloxycarbonyl, octadecyloxycarbonyl, icosyloxycarbonyl, formate, acetyloxy, propionyloxy, butyryloxy and the like.

Some representative compounds of Formula I are: bis(2, 6-di-tert-butylphenyl) perfluoromethylphosphite; 2,6-di-tert-butylphenyl perfluoroethylphosphite; bis(2,4-di-tert-butylphenyl) perfluoromethylphosphite; 2,4-di-tert-butylphenyl perfluoroethylphosphite; bis(4-(2-octa-decyloxycarbonylethyl)-2,6-di-tert-butylphenyl) perfluoromethylphosphite; (aka bis[2,6-di-tert-butyl-4-(2-carbooctadecyloxyethyl)phenyl]perfluoromethylphosphite); 4-(2-octadecyloxycarbonylethyl)-2,6-di-tert-butylphenyl perfluoroethylphosphite; bis(4-(2-dodecyloxycarbonylethyl)-2,6-di-sec-butylphenyl) perfluoromethylphosphite and the like.

The most preferred compounds in Formula I are: bis(2,6-di-tert-butylphenyl) perfluoromethylphosphite; bis(2,4-di-tert-butylphenyl) perfluoromethylphosphite and bis(4-(2-octadecyloxycarbonylethyl)-2,6- di-tert-butylphenyl) perfluoromethylphosphite.

The aromatic fluorophosphites of the invention are particularly useful as antioxidants. The antioxidants can be used in a broad range of organic material normally subject to gradual degradation in the presence of oxygen during use over an extented period. In other words, the organic materials protected by the present antioxidants are of the type in which the art recognizes the need for antioxidant protection and to which an antioxidant of some type is customarily added to obtain an extended service life. The oxidative degradation protected against is the deterioration of the organic composition during or after processing rather than, for example, combustion.

Examples of organic materials in which the antioxidants of this invention are useful include polymers, both homopolymers and copolymers, of olefinically unsaturated monomers, for example, polyolefins such as polyethylene, polypropylene, polybutylene and the like.

Also, polyhalohydrocarbons such as polyvinyl chloride, polychloroprene, polyvinylidene chloride, polyfluoroolefins, and the like, are afforded stabilization. The antioxidants provide antioxidant protection in natural and synthetic rubbers such as copolymers of olefinically unsaturated monomers including styrenebutadiene rubber (SBR rubber), ethylene-propylene copolymers, ethylene-propylene-diene terpolymers such as the terpolymer of ethylene, propylene and cyclopentadiene or 1,4-cyclooctadiene. Polybutadiene rubbers such as cis-polybutadiene rubber are protected. Poly-2-chloro-1,3-butadiene (neoprene) and poly-2-methyl-1,3-butadiene (isoprene rubber) are stabilized by the present additives. Likewise, acrylonitrile-butadiene-styrene (ABS) resins are effectively stabilized. Ethylene-vinyl acetate copolymers (EVA) are protected, as are butene-methylacrylate copolymers. Nitrogen-containing polymers such as polyurethanes, nitrile rubber, and lauryl acrylate-vinyl pyrrolidone copolymers are effectively stabilized. Adhesive compositions such as solutions of polychloroprene (neoprene) in toluene are protected. Polyphenylene ethers such as poly-2,6-dimethyl-1,4-phenylene ethers either alone or in combination with blending agents such synthetic rubbers are protected by the present invention. Likewise polystyrene and rubber modified polystyrene (i.e. high impact polystyrene) are stabilized.

Petroleum oils such as solvent-refined, midcontinent lubricating oil and Gulf Coast lubricating oils are effectively stabilized. In hydrocarbon lubricating oils, both mineral and synthetic, the present antioxidants are effective when used in combination with a zinc dihydrocarbyl dithiophosphate e.g. zinc dialkyl dithiophosphate or zinc dialkaryl dithiophosphate.

Synthetic ester lubricants such as those used in turbines and turbojet engines are given a high degree of stabilization. Typical synthetic ester lubricants include di-2-ethylhexyl sebacate, trimethylolpropane tripelargonate, $C_{5-9}$ aliphatic monocarboxylic esters of pentaerythritol, complex esters formed by condensing under esterifying conditions, mixtures of polyols, polycarboxylic acids, and aliphatic monocarboxylic acids and/or monohydric alkanols. An example of these complex esters is the condensation product formed from adipic acid, ethylene glycol and a mixture of $C_{5-9}$ aliphatic monocarboxylic acids. Plasticizers such as dioctyl phthalate are effectively protected. Heavy petroleum fractions such as tar and asphalt can also be protected should the need arise.

Polyamides such as adipic acid-1,6-diaminohexane condensates and poly-6-aminohexanoic acid (nylon) are effectively stabilized. Polyalkylene oxides such as copolymers of phenol with ethylene oxide or propylene oxide are stabilized. Polyphenyl ethers such as poly-2,6-dimethylphenyl ether formed by polymerization of 2,6-dimethylphenol using a copper-pyridine catalyst are stabilized. Polycarbonate plastics and polyformaldehydes are also protected.

Linear polyesters such as phthalic anhydride-glycol condensates, poly[ethylene terephthalate] (PET), and poly[butylene terephthalate] (PBT), are given a high degree of protection. Other polyesters such as trimellitic acid-glycerol condensates are also protected. Polyacrylates such as polymethylacrylate and polymethylmethacrylate are effectively stabilized. Polyacrylonitriles and copolymers of acrylonitriles with other olefinically unsaturated monomers such as methylmethacrylates are also effectively stabilized.

The antioxidants of the present invention are preferably used in either thermoset or thermoplastic polymer compositions. The thermoset polymers are those plastics which when subjected to heat, will normally become infusible or insoluble and as such cannot be remelted. They have elaborately cross-linked three dimensional structures and are used for plastics, elastomers, coatings and adhesives.

In contrast to the thermoset polymers, most thermoplastic polymers can be made to soften and take a new shape by the application of heat and pressure. Thermoplastic polymers comprise long-chain molecules often without any branching (e.g., high density polyethylene). Thermoplastic polymers normally are rigid at operating temperatures, but can be remelted and reprocessed. They include polyethylene, polycarbonate, polypropylene, polystyrene, polyvinyl chloride, acrylonitrile-butadiene-styrene (ABS), nylon, and the like, including polymers intended for high temperature applications. The most preferred organic compounds intended for the practice of the present invention are polypropylene and polyethylene.

The more preferred utility of the new additives is in the stabilization of thermoplastic polymers during processing such as during extrusion. Of these the most preferred polymers are polyethylene, polypropylene, linear low density polyethylene and polycarbonates.

The antioxidants of the present invention are useful to control oxidative and color degradation of resins used as tackifiers in adhesives. The resin which can be protected include synthetic hydrocarbon resins, such as cycloaliphatic $C_5$ resins, aromatic $C_9$ resins, terpene resins and the like. Also included are natural resins, such as wood rosin, gum rosin and toll oil rosin which are processed for tackifier applications.

The antioxidants are incorporated into the organic material in a small but effective amount so as to provide the required antioxidant protection. A useful range is generally from about 0.005 to about 5 weight percent of organic material, and a preferred range is from about 0.01 to 2 weight percent.

Methods of incorporating the antioxidants into the organic material are well known. For example, if the material is liquid, the additive can be merely mixed into the material. Solid organic materials can be merely sprayed with a solution of the additive in a volatile solvent. For example, stabilized grain products result from spraying the grain with a toluene solution of the antioxidant. In the case of rubbery polymers, the additive can be added following the polymerization stage by mixing it with the final emulsion or solution polymerization mixture and then coagulating or removing solvent to recover the stabilized polymer. It can also be added at the compounding stage by merely mixing the additive with the rubbery polymer in commercial mixing equipment such as a Banbury blender. In this manner, rubbery polymers such as styrene-butadiene rubber, cis-polybutadiene or isoprene polymers are blended with the antioxidant together with the other ingredients normally added such as carbon black, oil, sulfur, zinc oxide, stearic acid, vulcanization accelerators, and the like. Following mastication, the resultant mixture is fabricated and molded into a finished form and vulcanized.

In making compounds of the present invention, a phenol is reacted with $PCl_3$ or $PBr_3$ to form a chloro or bromophosphite intermediate which is then reacted with a fluorinating agent as shown in the following equations.

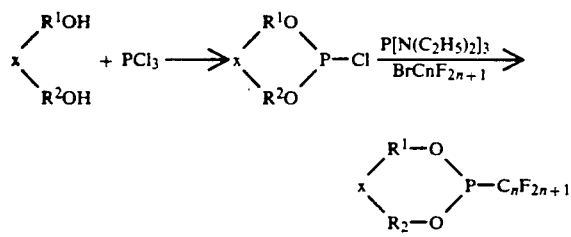

In the above illustration, $PCl_3$ is used but $PBr_3$ could also be used.

The amount of $PCl_3$ or $PBr_3$ used to form the intermediate chloro or bromophosphite typically depends on the number of hydroxyl groups in the phenolic reactant and the average number of residual P-Cl or P-Br groups desired in the intermediate. For example, if two moles of monohydroxy phenolic compound are reacted with one mole of $PCl_3$ the average intermediate compound will be a monochlorophosphite. When one mole of an ortho-ortho bridged diphenol is reacted with one mole of $PCl_3$, the major component in the intermediate will be a cyclic monochlorophosphite such as may be used to make the fluorophosphites of the present invention.

The starting phenolic compounds are well known and described in the literature such as in U.S. Pat. Nos. 2,836,577; 2,944,986; 3,562,338; 1,972,599; 2,807,653; 3,449,441; 1,892,990; 2,394,754; 2,479,948; 2,905,674; 3,367,980; 3,069,384; 2,202,877; 2,313,782; 3,065,275; 2,841,619; 2,315,556; 2,469,469; 2,836,609; 3,146,273; 2,008,032; 2,714,120; 3,093,587; 3,060,121; 2,538,355; 2,364,338; 3,330,859; 3,062,896; 3,026,264; 3,531,483; J.A. Chem. Soc. 78 1069 (1956) and others.

The reaction of the $PCl_3$ or $PBr_3$ with the phenol is, preferably conducted in an aprotic solvent such as THF, benzene, toluene, xylene, heptane, octane, cyclohexane and the like. The reaction can also be conducted in an excess of $PCl_3$ or $PBr_3$ which functions as a solvent or reaction medium. The reaction temperature should be high enough to cause the reaction to proceed at a reasonable rate but not so high as to cause decomposition. A useful temperature range is from $-30°$ to $300°$ C. A preferred temperature range is $0°-100°$ C. and a more preferred temperature range is about $25°-75°$ C. and most preferably at reflux temperature.

The chloro or bromophosphite intermediate is fluorinated by reaction with at least an equivalent amount of the fluorinating agent based on the equivalent of Cl and/or Br bound to phosphorus. An excess can be used. The fluorination is preferably conducted in a aprotic solvent. The reaction can be conducted in the same reaction mixture resulting from the preparation of the intermediate.

The fluorination temperature should be high enough to cause the fluorine to replace the chlorine or bromine but not so high as to cause decomposition. A useful temperature range is about $-75°-0°$ C., more preferably $-70°$ -to $-15°$ C. and most preferably at $-65°$ to $-50°$ C.

The aromatic fluorophosphites of the present invention may be used alone as the antioxidant or may be used in combination with phenolic antioxidants, thioesters such as dilauryl thiodipropionate and distearyl thiodipropionate, light stabilizers such as hindered amines or ultraviolet light absorbers, metal deactivators, pigments, dyes, lubricants such as calcium stearate, nucleation agents and talc and other fillers.

Some representative examples of useful UV stabilizers are:

UV Stabilizers

Nickel dibutyldithiocarbamate
2-hydroxy-4-n-octyloxybenzophenone
2,4-di-tert-butylphenyl 3,5-di-tert-butyl-4-hydrozybenzoate
Nickel bis[o-ethyl(3,5-di-tert-butyl-4-hydroxybenzyl) phosphonate
2-(3',5'-di-tert-butyl-2'-hydroxyphenyl-5-chlorobenzotriazole
Bis(2,2,6,6-tetramethyl-piperridinyl-4)sebacate
Bis(1,2,2,6,6-pentamethyl-piperridinyl-4)sebacate
n-Butyl-(3,5-di-tert-butyl-4-hydroxybenzyl)-bis (1,2,2,6,6-pentamethyl-4-piperridinyl)malonate
Dimethyl succinate polymer with 2,2,6,6-tetramethyl-1-piperridineethanol
N,N'-bis(2,2,6,6-tetramethyl-4-piperridinyl)-1,6-hexane diamine, polymer with 2,4,6-trichloro-1,3,5-triazine and 2,4,4-trimethyl-1,2-pentanamine
polymeric hindered amines such as Gasorb UV3346 (American Cyanamid); Spinuvex A-36 (Montedison); Chimassorb 944 (Ciba-Geigy)
2-(2'-hydroxy-3',5'-di-tert-amylphenyl)benztriazole
2,2'-thiobis(4-tert-octylphenolato)butylamino-Nickel-(II)
Nickel bis((ethyl-(3,5-di-tert-butyl-4-hydroxybenzyl)-phosphonate)
and the like.

Phenolic antioxidants which are suitable for use in the present invention are well known in the art and include 2,6-di-t-butyl-4-methylphenol; 2,6-di-t-butyl-4-methoxymethylphenol; 2,6-dioctadecyl-4-methylphenol; 3,5-di-t-butyl-4-hydroxyanisole; 2,5-di-t-butyl-4-hydroxyanisole; 4-(hydroxymethyl)-2,6-di-t-butylphenol; 4,4'-methylenebis(2,6-di-t-butylphenol); 2,2'-ethylidenebis (4,6-di-t-butylphenol); 4,4'-thiobis(2-methyl-6-t-butylphenol); tetrakis(methylene 3-(3,5-di-t-butyl-4-hydroxyphenyl)propionate)-methane; 1,3,5-tris(3,5-di-t-butyl-4-hydroxybenzyl)isocyanurate; 0,0'-di-n-octadecyl(3,5-di-t-butyl-4-hydroxybenzyl)phosphonate; octadecyl 3-(3,5-di-t-butyl-4-hydroxyphenyl)propionate; 2,2'-oxamidobisethyl 3-(3,5-di-t-butyl-4-hydroxyphenyl)-propionate; calcium bis(0-ethyl(3,5-di-t-butyl-4-hydroxybenzyl)phosphonate) and mixtures thereof. A particularly preferred phenolic antioxidant is 1,3,5-trimethyl-2,4,6-tris(3,5-di-t-butyl-4-hydroxybenzyl)benzene which is available from Ethyl Corporation as Ethanox TM -330 Antioxidant.

When utilized, the phenolic antioxidants are preferably present with the aromatic fluorophosphites in an amount in the range of from about 0.005 to about 3.0 percent by weight based on the weight of the total composition.

The following examples are presented to illustrate certain specific embodiments of the invention, but are not intended to be construed so as to be restrictive of the spirit and scope thereof.

EXAMPLE 1

2,2'-Ethylidenebis (4,6-di-tert-butylphenyl) trifluoromethylphosphonite

A flask equipped with a dry ice condenser was flame dried under a nitrogen stream, and charged with 12g (24 mmol) of 2,2'-ethylenebis(4,6-di-tert-butylphenyl)-chlorophosphonite and 80 mL of dichloromethane. After cooling the resulting mixture to −78° C. and charging the condenser with dry ice and acetone, 6.8 mL of bromotrifluoromethane (Freon 13B1) that had been condensed into a graduated tube was warmed to room temperature and allowed to distill into the flask. The cold bath was replaced by an insulating bath and the mixture was allowed to reach the temperature of the refluxing freon (−59° C.). Then 9.3 mL (34 mmol) of hexaethylphosphorous triamide was added dropwise. The mixture was stirred cold for 1 hour and the condenser was removed to allow excess freon to distill away. The mixture was recooled to 0-5° C. and filtered at this temperature. The filter cake was washed with 30 mL of ice-cold dichloromethane, triturated in 100 mL of refluxing dichlormethane, and filtered. Reduction in volume (to about 50 mL) and cooling of the mother liquor afforded 3.3 g of white, crystalline solid. Gas chromatographic analysis of this indicated it was 96% compound 2,2'-ethylenebis(4,6-di-tert-butylphenyl)trifluoromethylphosphonite 4% compound 2,2'-ethylenebis(4,6-di-tert-butylphenyl)chlorophosphonite (about 24% yield).

The antioxidant effectiveness of AN-1130 was compared to X-398 (FDA sample) and ETHANOX 330 Antioxidant. Compositions of 330/phosphite/CaSt at 1000/500/100 ppm were extruded at 30 rpm and 288° C. (550° F.) barrer temperature.

The performance of AN-1130 in PP is slightly superior on color hold but inferior on melt flow control than X-398. See Table II.

TABLE I

Testing 2,6-di-tert-butyl-4-trifluoromethylphenol in New Technology Polypropylene-Profax 6501

| Stabilization Formula: | Antioxidant - 1000 ppm<br>Calcium Sterate - 100 ppm |
| --- | --- |
| Twin Screw Temp. Profile: | Zones #1-150° C., #2&3-245° C. and 30 rpm |
| Single Screw Temp. Profile: | All zones 260° C. (500° F.) and 30 rpm |

| Stabilization System | MFI at 230° C. - 2160 Load Extrusion Passes | | | | Yellow Index Extrusion Passes | | |
| --- | --- | --- | --- | --- | --- | --- | --- |
| | TWS | 1 | 3 | 5 | TWS | 1 | 5 |
| Profax 6501/CaSt | 3.2 | 5.9 | 11.4 | 20.4 | 3.7 | 5.0 | 7.4 |
| 330/CaSt | 2.7 | 3.9 | 4.9 | 7.0 | 3.6 | 6.2 | 10.6 |
| AN-1129/CaSt | 2.7 | 4.3 | 5.5 | 6.7 | 3.3 | 5.7 | 9.7 |
| BHT/CaSt | 2.8 | 3.3 | 4.4 | 5.4 | 3.2 | 4.5 | 8.3 |

TABLE II

Testing New Fluorophosphite in New Technology Polypropylene-Profax 6501
Stabilization Formula: ETHANOX 330 Antioxidant - 1000 ppm
Fluorophosphite - 500 ppm Calcium Sterate - 100 ppm
Twin Screw Temp. Profile: Zones #1-150° C., #2&3-245° C. and 30 rpm
Single Screw Temp. Profile: All zones 288° C. and 30 rpm

| Stabilization System | MFI at 230° C. - 2160 Load Extrusion Passes | | | | | Yellow Index Extrusion Passes | | |
| --- | --- | --- | --- | --- | --- | --- | --- | --- |
| | TWS | 1 | 3 | 4 | 5 | TWS | 1 | 4 | 5 |
| 330/CaSt | 4.1 | 7.4 | 14.8 | 19.7 | | 3.6 | 7.8 | 12.8 | |
| X-398/FDA/330/CaSt | 3.4 | 5.0 | 9.9 | | 17.0 | 3.3 | 5.7 | | 11.8 |
| AN-1130/330/CaSt | 3.7 | 6.6 | 12.8 | | 20.7 | 3.4 | 5.5 | | 9.7 |

I claim:

1. An aromatic fluoroalkylphosphorous compound suitable for use as an antioxidant said compound having the structure

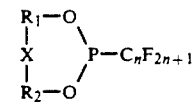

wherein $R_1$ and $R_2$ are the same or different and are substituted or unsubstituted aryl groups, wherein the substituents are selected from the group consisting of alkyl, aryl, aralkyl, cycloalkyl, hydroxy, alkoxy, aryloxy and halo; X is a single bond connecting $R_1$ and $R_2$, or X is selected from the group consisting of $C_1$ to $C_{12}$ linear or branched alkylene, —O— or —$S_g$— where g is an integer from 1 to 3; and n is an integer from 1 to 8.

2. A compound according to claim 1 wherein $R_1$ and $R_2$ are the same and are substituted aryl.

3. A compound according to claim 2 wherein the substituent is alkyl.

4. A compound according to claim 1 wherein X is $C_1$ to $C_{12}$ linear or branched alkylene.

5. A compound according to claim 4 wherein X is $C_1$ to $C_6$ linear or branched alkylene.

6. A compound according to claim 1 wherein n is an integer from 1 to 4.

7. A compound according to claim 1 wherein $R_1$ and $R_2$ are the same and are aryl substituted with at least one tert-butyl group, X is $C_1$ to $C_6$ branched alkylene and n is an integer from 1 to 4.

8. A compound according to claim 7 wherein X is the group $CH_3$—CH— and n is 1.

9. Organic material normally susceptible to gradual degradation when in contact with oxygen, said organic material containing an antioxidant amount of an aromatic fluoroalkylphosphorous compound having the following structure,

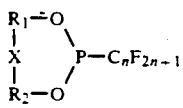

wherein $R_1$ $R_2$ are the same or different and are substituted or unsubstituted aryl groups, wherein the substituents are selected from the group consisting of alkyl, aryl, aralkyl, cycloalkyl, hydroxy, alkoxy, aryloxy and halo; X is a single bond connecting $R_1$ and $R_2$, or X is selected from the group consisting of a $C_1$-$C_{12}$ linear or branched alkylene, —O—, or —$S_g$— where g is an integer from 1 to 3; and n is an integer from 1 to 8.

10. An organic composition according to claim 9 wherein $R_1$ and $R_2$ are the same and are substituted aryl.

11. An organic composition according to claim 10 wherein the substituent is alkyl.

12. An organic composition according to claim 9 wherein X is $C_1$ to $C_{12}$ linear or branched alkylene.

13. A organic composition according to claim 12 wherein X is $C_1$ to $C_6$ linear or branched alkylene.

14. A organic composition according to claim 9 wherein n is an integer from 1 to 4.

15. A organic composition according to claim 9 wherein $R_1$ and $R_2$ are the same and are aryl substituted with at least one tert-butyl group, X is $C_1$ to $C_6$ branched alkylene and n is an integer from 1 to 4.

16. A organic composition according to claim 15 wherein X is the group $CH_3$—CH— and n is 1.

* * * * *